United States Patent [19]

Aspisi et al.

[11] 4,436,874

[45] Mar. 13, 1984

[54] ACRYLIC COPOLYMERS AND THEIR USE IN SOLID PHASE PEPTIDE SYNTHESIS

[75] Inventors: Christian Aspisi, Boulgon; Bernard Calas, Saint-Gely du Fesc; Jacques Daunis, Montpellier; Michel Follet, Aramon; Robert Jacquier; Joseph Parello, both of Montpellier, all of France

[73] Assignee: Societe d'Expansion Scientifique "EXPANSIA", Paris, France

[21] Appl. No.: 440,440

[22] Filed: Nov. 10, 1982

[30] Foreign Application Priority Data

Nov. 19, 1981 [GB]  United Kingdom ............... 8134861

[51] Int. Cl.$^3$ .................... B01J 31/08; C08F 220/58; C08F 220/60
[52] U.S. Cl. ................................ 525/327.1; 526/304; 521/32; 525/382; 525/326.7; 525/374
[58] Field of Search ................. 526/304; 525/327.1, 525/382, 326.7, 374; 521/32

[56] References Cited

U.S. PATENT DOCUMENTS

| | | | |
|---|---|---|---|
| 2,845,408 | 7/1958 | Melamed | 526/304 |
| 3,069,390 | 12/1962 | Kline | 526/304 |
| 3,821,126 | 6/1974 | Yamamoto et al. | 54/32 |
| 3,965,070 | 6/1976 | Wuchter | 521/32 |

OTHER PUBLICATIONS

International Journal of Peptide and Protein Research, vol. 15(4), 1980, pp. 331–334 Stahl et al.

*Primary Examiner*—Joseph L. Schofer
*Assistant Examiner*—Peter F. Kulkosky
*Attorney, Agent, or Firm*—Eyre, Mann, Lucas & Just

[57] ABSTRACT

The present invention relates to new amino-functionalized acrylic copolymers, their preparation and their use in peptide synthesis.

6 Claims, No Drawings

ACRYLIC COPOLYMERS AND THEIR USE IN SOLID PHASE PEPTIDE SYNTHESIS

This invention concerns new acrylic copolymers, and their use in solid phase peptide synthesis.

The new copolymers covered by the invention are derived from those described by the applicant in a previous patent application, by functionalization using ethylenediamine. The copolymers covered by the previous application, indicated by A or P—$COR_3$, with $R_3$=H or —$CH_3$, were obtained by the copolymerization of the following three monomers:

I. A monomer is defined as the support (matrix) and is an N-acryloylpolymethyleneimine, of the formula:

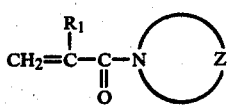

with $R_1$ = H or —$CH_3$
$Z$ = —$(CH_2)_{n1}$— with $n_1$ = 4, 5 or 6 or

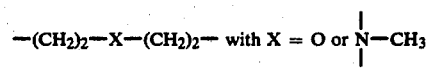
—$(CH_2)_2$—X—$(CH_2)_2$— with X = O or N—$CH_3$ or an N-acryloyldialkylamide, with the formula:

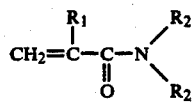

with $R_1$ having the same meaning as above and $R_2$=—$CH_3$ or —$C_2H_5$

II. A monomer defined as the reticulation agent (linker) and which is an N,N'-bisacryloyldiaminoalcane of the formula:

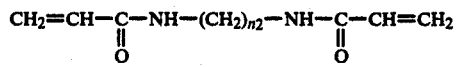

with $n_2$ = 1 or 2

III. A monomer defined as the functionalization agent and which is an N-acryloylaminoacid or ester, of the formula:

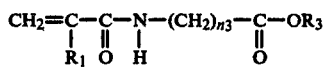

with $R_1$ as above $R_3$ as $R_1$ and $n_3$=1, 2, 3 or 5 or an asymmetrical N-acryloylaminoacid (or esters), of the L series, of the formula:

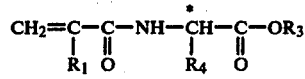

with $R_1$ and $R_3$ having the same meaning as above and $R_4$ = —$CH_3$

-continued

—$CH(CH_3)_2$

—$CH_2(CH_3)_2$

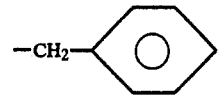

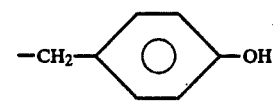

—$CH_2$—$CH_2$—S—$CH_3$

—$(CH_2)_4$—$NH_2$ or, further, the N-acryloyl-L-proline, or its methylic ester of the formula:

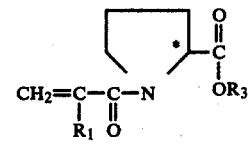

with $R_1$ and $R_3$ having the same meaning as above.

The functionalization to obtain the copolymers covered by the invention involves creating an extension by amidification with ethylenediamine, to give B:

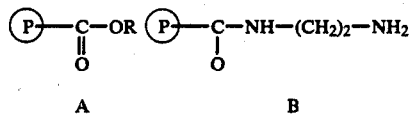

This amidification may be achieved by one of the following routes:

(a) using the acid function (A, $R_3$=H), by coupling with one of the reagents normally used in literature: dicyclohexylcarbodiimide (DCC) in the presence of an activation agent, such as 1-hydroxy benzotriazole (HOBt), BOP reagent etc.

(b) using the ester function (A, R=$CH_3$), by stirring the resin at room temperature, with an excess of anhydrous ethylene diamine.

A systematic study of the experimental conditions for the second method has resulted in the reduction of a secondary bridging reactions while maintaining 90% of the initial functionalization degree.

The solid phase peptide synthesis method, developed in 1962, mainly using polystyrene type supports (Merrifield's resin, benzhydrylamine resin, alcoxybenzylic resin, PAM resin, etc.), is very well known and has been developed considerably (for example: Erickson and Merrifield, in Neurath and Hill, The Proteins, Vol. 2, Academic Press, 1976, p. 255; BIRR, Aspects of the Merrifield Peptide Synthesis, Springer, 1978; BARANY and MERRIFIELD, in GROSS and MEIENHOFER, The Peptides: Analysis, Synthesis, Biology, Vol. 2, Part A, Academic Press, 1980, P. 1). The resin, suitably functionalized is esterified or amidified by an N-protected aminoacid, located on the C-terminal position in the peptide to be synthesized. After deprotection of the amino groupe the coupling is performed, using one of the many methods described in the literature, with an N-protected aminoacid located on the penultimate position in the synthesized sequence. These operations are repeated until the required peptide sequence is obtained on the resin. In the last stage, the peptide is separated from its support.

This method offers definite advantages in relation to synthesis in solution: in particular, the process is very simple and fast (it is no longer necessary to isolate and purify the peptides after each coupling). Excess reagents and impurities are easily eliminated by filtering and washing the support and there is no, or very little, racemization. However, the process has one disadvantage, in that for each coupling, a practically quantitative output is required, as each incomplete reaction would result in an accumulation of truncated peptide sequences which would contaminate the final product. This means that considerable excesses of reagents must be used and each coupling operation must be repeated until a suitable analytical test (for example, ninhydrine), indicates that all free $NH_2$ function has disappeared from the resin. However, these experimental conditions become somewhat dissuasive when the synthesis requires the use of non naturally existing aminoacids, which may be rare and expensive.

In order to obtain the maximum advantage from the homogeneous phase reactions, it has been proposed that soluble polymers be used (MUTTER and BAYER, in GROSS and MEIENHOFER, The Peptides: Analysis, Synthesis, Biology, Vol. 2, Part A, Academic Press, 1980, p. 285), and, particularly polyethyleneglycol. However, this technique has not been widely used, probably due to the experimental problems caused by:

reduced solubility which may accompany the extension of the peptide sequence.

isolation of the support after each coupling, requiring an ultrafiltration step. (MUTTER, HAGENMAIER and BAYER, Angew. Chem. Int. Ed., 1971, 10, 811; BAYER, GATFIELD, MUTTER and MUTTER, Tetrahedron, 1978, 34, 1829) or crystallization by addition of ether, followed by elimination of the solvent, as required (BAYER and MUTTER, Chem. Ber., 1974, 107, 1344; MUTTER, UHMANN and BAYER, Ann. Chem., 1975, 901; CORRING and JUNG, Ann. Chem., 1975, 1965 and 1776)

separation of the peptide from its support (TJOENG, TONG and HODGES, J. Org. Chem. 1978, 43, 4190; TJOENG and HODGES, Tetrahedron Letters, 1979, 1273; MUTTER, BAYER and GATFIELD, J. Org. Chem., 1980, 45, 5364).

The same difficulties occur in the case of polystyrene base soluble supports, which are slightly reticulated or not reticulated, thus requiring filtering of the gel (BIRR, in "Peptides 1972", North Holland Publ., 1973, p. 72; Andrhatta and Rink, Helv. Chim. Acta, 1973, 56, 1205) or precipitation by alcohol (Narita, Bull. Chem. Soc. Japan, 1978, 51, 1477).

Finally, the alternate liquid phase—solid phase technique (Frank, Meyer and Hagenmaier, Chem. Zeit., 1977, 101, 185) has also not been widely developed.

More recently, the superiority of polyacrylic supports, such as Walter's PAP (J. Amer. Chem. Soc., 1979, 101, 5383) and Sheppard's resin (JCS Perkin I, 1981, p. 529 and 538), which possess the property of swelling in a much wider range of solvents than do styrene polymers, has been clearly demonstrated (Atherton, Gait, Sheppard and Williams, Biorg. Chem. 1979, 8, 774) easier separation of the polypeptide and its support at the end of the synthesis, and greater compatibility between the solvent requirements of the support and those of the growing peptide moieties, which reduces aberrant truncation and coupling. The favourable influence of the resin peptide solvent compatibility on the coupling yields has been demonstrated (ATHERTON, WOOLLEY and SHEPPARD, Chem. Comm. 1980, p. 970). However, the comments already made in the case of the polystyrene resins, concerning the use of a considerable reagent excess (of the order of 2.5 times) and the necessity to generally repeat each coupling operation several times, remain valid. In this respect, it is significant that recent, long sequence polypeptide synthesis still use the solution method (for example, KENNER, RAKAGE and SHEPPARD, Tetrahedron, 1979, 35, 2767, NAGARAJ and BALARAN, Tetrahedron, 1981, 37, 1263; FUJII and YAJIMA, JCS Perkin I 1981, p. 789, 787 and 804).

In order to counter the effects of the different solvent requirements of the matrix and the growing polypeptide sequence, mentioned above, a new polyacrylamide gel has recently been proposed (R. EPTON and A. WILLIAMS, Int. J. Biol. Macromol. 1981, 3, 334). For this, the functionalization agent is a phenolic derivative and constitutes the main part of the matrix. This gel therefore behaves physically as a pseudo solution.

Conversely, the amino-acid couplings occur on the phenolic part of the resin. Due to steric hindrance, these couplings are not quantitative and at each stage, acetylation is required to avoid side reactions. Steric hindrance is such that this type of resin can only be applied to the short peptide synthesis. Finally, the last deprotection requires an extended period of boron trifluoride treatment (several days).

As will be seen below, the supports covered by this invention considerably simplify and improve the solid phase peptide synthesis conditions.

In order to carry out peptide synthesis according to the invention, resin modification is to be effected by introducting a reversible anchor system. As a non-limiting example, it is possible to use the C-type reagent (MITCHELL, ERICKSON, RYABSTEV, HODGES and MERRIFIELD, J. Amer. Chem. Soc. 1976, Stahl, Walter and Smith, J. Amer. Chem. Soc. 1979, 101, 5383; ATHERTON, LOGAN and SHEPPARD, JCS Perkin I, 1981, p. 538; ATHERTON, HUBSCHER, SHEPPARD and WOOLLEY, 2. Physiol. Chem. 1981, 362, 833)

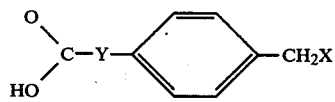

in which
X=Cl, Br or OH
Y may represents a —$CH_2$—O group or —$CH_2$ group.
The reaction between B and C, to give D:

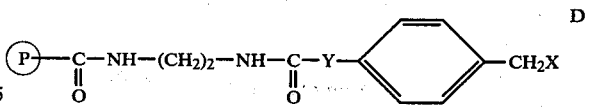

may be performed practically quantitatively, using one of the previously mentioned coupling agents, or by the action of II on an activated ester (prepared with trichloro-2,4,5 phenol, pentachlorophenol, ...) of III, in the presence of, or without, a catalyst (HOBT, ...)

Another reversible anchor system may be obtained using an E type reactive (R=H or CH$_3$) (Mzoguchi, Shigezan and Takamura, Chem. Pharm. 1970, 18, 1465; Wang, J. Org. Chem. 1976, 41, 3258) which is condensed with B to give F.

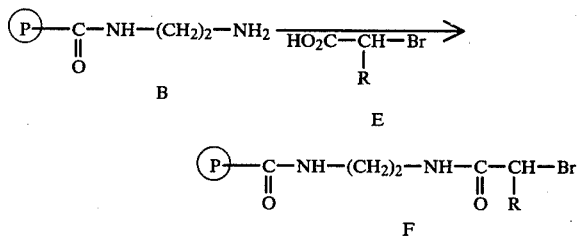

The fixation of the final aminoacid C in the first stage, and the final separation of the peptide from its support, are achieved under the same conditions as those described above.

The resins thus functionalized and used in peptide synthesis have a functionalization level between 0.2 and 5 meq per gram and preferably between 1.0 and 1.2 meq per gram.

The fixation on the resin, of the C-terminal aminoacid, the NH$_2$ of which is protected, for example, by a labile-acid t-butyloxycarbonyle group (Boc) or by the labile-alkaline fluorenylmethyloxycarbonyle group (Fmoc), may be achieved by several routes:

using caesium salt when X=Cl or Br by action of dicyclohexylcarbodiimide (DCC) in the presence of 4-dimethylamino pyridine (DMAP) as a catalyst when X=OH, or, when X=OH, by preparing extemporaneously the symmetrical anhydride of the N-protected aminoacid, and allowing it to react with D in the presence of DMAP. The final separation of the peptide from its support is achieved:

by the action of a diluted mineral base solution, when Y is a methylene group or when F is used; with NH$_3$/CH$_3$OH it is possible to get a C-terminal amide, or, by the action of a diluted organic acid (trifluoroacetic acid, ...) solution, when Y represents a —CH$_2$—O— group.

Peptide synthesis procedure

The supports covered by the invention have the property of offering good permeability and swelling notably in a wide range of protic and aprotic solvents, as well as in aqueous buffer solution of varied pH.

Under these conditions, during coupling, the resin carrying the N-Boc or C-terminal aminoacid N-Fmoc (or peptide being prepared and suitably protected) behaves as a "pseudo-solution" and the gel thus formed cannot be filtered. This creates particularly favourable conditions, close to those of the homogeneous phase for the peptide bond formation. When the reaction is terminated, the addition of a third solvent (ether, THF, dioxane, ...) provokes the expulsion of the solvent in the resin and the precipitation of the same in a form which is easily and quickly filtered, which is not the case when using known techniques.

These particular and specific properties of the resins covered by the invention result in a significant increase in speed (by a factor of at least three, in relation to known techniques), and yield of the couplings. For each individual coupling, this allows a considerable decrease in the value of the ratio: number of N-protected aminoacid moles/support functionalization level (1.1 to 1.2, whereas usual current values are of the order of 2.5). In addition, there is no column clogging during intermediate filterings.

Alternation of quasi-homogeneous phase coupling and and support precipitation thus constitutes a new, simplified and improved process for solid phase peptide synthesis.

As an example, coupling operation procedure may be as follows:

1. Addition of a chloride solvent (CHCl$_3$, CH$_2$Cl$_2$ ...) to swell the resin carrying the C-terminal aminoacid N-Boc (or the peptide suitably protected);
2. Washing, using linear or cyclic ether (ethylic ether, isopropylic THF, dioxane ...);
3. Addition of trifluoroacetic acid, in the solvent, for the deprotection of the NH$_2$;
4. Precipitation of the resin by addition of ether, as in 2
5. Filtering followed by four washings in ether, as in 2;
6. Neutralization by addition of diisopropylethylamine in the chlorinated solvent;
7. Four washings in ether, as in 2, followed by drying in a nitrogen flow;
8. Coupling by stirring with a solution of symmetrical anhydride prepared extemporaneously of an N-Boc aminoacid, in the chlorinated solvent;
9. Precipitation by addition of ether, as in 2, and filtering, and
10. Four washings in ether, as in 2.

This new procedure was successfully tested in the synthesis of biologically interesting peptides, for example, a undecapeptide Ac-Gly-Gly-Lys-Gly-Gly-Ala-Arg-Lys-Val-Leu-Homo Ser.

EXAMPLE

Peptide synthesis
Ac-Gly-Gly-Lys-Gly-Gly-Ala-Arg-Lys-Val-Leu-Homo Ser

The peptide is synthesized on an acrylic resin obtained by copolymerizing the N-acryloylpyrrolidine, ethylenebisacrylamide and the N-acrylic derivative of the methyl ester of aminocaproic acid. The support is then functionalized as follows: 32 ml of redistilled ethylenediamine are added to 1 g of resin (functionalized by CO$_2$CH$_3$) and this is stirred for one night, at room temperature. The mixture is then filtered, washed in demineralized water until neutrality is obtained, and then washed in ethanol and ether. The resin is finally dried for 24 hours under reduced pressure. It then contains 1 meq of NH$_2$ per gram of dry polymer.

2 g of resin was used, i.e. 2 meq of NH$_2$. The operating cycle required to attach aminoacid to the resin is as follows:

| Solvent or reactive | N° | Reaction | Volume (ml) | Time (mn) |
|---|---|---|---|---|
| Anhydrous diethyl ether | 1 | rinsing | 75 | 2 |
| — | 2 | — | — | — |
| — | 3 | — | — | — |
| — | 4 | — | — | — |
| Trifluoroacetic acid | 5 | deprotection | 50 | 2 |

-continued

| Solvent or reactive | N° | Reaction | Volume (ml) | Time (mn) |
|---|---|---|---|---|
| 30/CH$_2$Cl$_2$70 (V/V) | | | | |
| — | 6 | — | 50 | 30 |
| Anhydrous diethyl ether | 7 | rinsing | 75 | 2 |
| — | 8 | — | — | — |
| — | 9 | — | — | — |
| — | 10 | — | — | — |
| Diisopropylethylamine 10/CH$_2$Cl$_2$90 (V/V) | 11 | neutralization | 50 | 2 |
| — | 12 | — | — | — |
| Anhydrous diethyl ether | 13 | rinsing | 75 | 2 |
| — | 14 | — | — | — |
| — | 15 | — | — | — |
| — | 16 | — | — | — |
| Addition of symetrical anhydride of aminoacid for coupling in 50 ml of CH$_2$Cl$_2$ | 17 | coupling | 50 | 60 |
| Anhydrous diethyl ether | 18 | mixing | 75 | 2 |
| — | 19 | — | — | — |
| — | 20 | — | — | — |
| — | 21 | — | — | — |
| Diisopropylethylamine 10/CH$_2$Cl$_2$90 (V/V) | 22 | neutralization | 50 | 2 |
| — | 23 | — | — | 30 |
| Anhydrous diethyl ether | 24 | rinsing | 75 | 2 |
| — | 25 | — | — | — |
| — | 26 | — | — | — |
| — | 27 | — | — | — |
| Addition of symmetrical anhydride of aminoacid for coupling in 50 ml of CH$_2$Cl$_2$. | 28 | coupling | 50 | 30 |
| Anhydrous diethyl ether | 29 | rinsing | 75 | 2 |
| — | 30 | — | — | — |
| — | 31 | — | — | — |
| — | 32 | — | — | — |

Checking of the coupling process is made by Kaiser's ninhydrine test.

As described in the experimental process, two couplings have been made for each aminoacid used. The coupling reaction is obtained using symmetrical anhydrides, which are prepared as follows: 1 mmol of protected aminoacid is dissolved in 2 ml of anhydrous CH$_2$Cl$_2$. The solution is cooled to 0° C. and 0.5 mmol of dicyclohexylcarbodiimide is added to the solution, in 10 ml of CH$_2$Cl$_2$. After 20 minutes reaction at 0° C., the dicyclohexylcarbodiimide precipitate is rinsed with 20 ml of CH$_2$Cl$_2$, and the solutions are mixed and placed in contact with the resin, in the reactor.

This method has allowed us to prepare the symmetrical anhydrides using Boc Gly OH, N$^\epsilon$ Z N$^\alpha$ Boc Lys OH Boc Val OH, Boc Leu OH, Boc Met OH, et Ac Gly OH. In the case of the N$^G$ NO$_2$, N$^\alpha$ Boc Arg OH, the product is dissolved in the minimum of DMF and the volume is brought to 20 ml with dry methylene chloride. The reaction then occurs, as described above. After the coupling of the last aminoacid, the resin is dried under reduced pressure in the presence of P$_2$O$_5$, for 24 hours, then suspended in 50 ml of trifluoroacetic acid. A slow current of dry HBR is then bubbled through the solution for two hours. The mixture is then abundantly rinsed with CH$_2$Cl$_2$ and Et$_2$O. This acidolysis deprotects the side chains of the lysines.

The orange-red powder obtained is then suspended in 100 ml of trifluoroacetic acid 2 M and 5 g of powdered zinc is added. After two hours' stirring at room temperature, the reacting mixture is abundantly washed with HCl (2 N), water, ethanol, and finally with anhydrous diethyl ether. This hydrogenolysis breaks the nitro group on the guanidium group of arginine.

After the resin has been dried under reduced pressure and P$_2$O$_5$, for 12 hours, 1 gram of polymer is extracted, which is treated with 2.5 grams of cyanogen bromide in 70 ml of propionic acid. After 24 hours' reaction at room temperature, the solution is liophylized and the desired peptide is obtained with a yield of 45%.

We claim:

1. New amino-functionalized acrylic copolymers derived by functionalization by ethylene diamine on R$_3$ substituent of the copolymers containing:

from 30% to 90%, by weight, of a monomer (matrix) corresponding to an N-acryloylpolymethylenimine of formula $$CH_2=\overset{R_1}{\underset{}{C}}-\underset{\underset{O}{\|}}{C}-N\diagup\!\!\!\diagdown Z \quad \text{with } R_1 = H \text{ or } -CH_3$$

$$Z = -(CH_2)_{n_1}- \text{ with } n_1 = 4, 5 \text{ or } 6 \text{ or}$$

$$-(CH_2)_2-X-(CH_2)_2- \text{ with } x = O \text{ or } \overset{|}{\underset{|}{N}}-CH_3$$

or a N-acryloyldialkylamide, of formula:

$$CH_2=\overset{R_1}{\underset{}{C}}-\underset{\underset{O}{\|}}{C}-N\diagdown\!\!{R_2 \atop R_2}$$

with
R$_1$ having the same meaning as above
R$_2$ = —CH$_3$ or —C$_2$H$_5$ from 2% to 50%, by weight, of a monomer (linker) corresponding to an N,N'-diacryloyldiaminoalcane of formula $$CH_2=CH-\underset{\underset{O}{\|}}{C}-NH-(CH_2)_{n_2}-NH-\underset{\underset{O}{\|}}{C}-CH-CH_2$$

with n$_2$ = 1 or 2 and from 2% to 65%, by weight, of a monomer (functionalization agent) corresponding to an acryloylaminoacid or ester, racemic of formula:

$$CH_2=\underset{R_1}{\overset{}{C}}-\underset{\underset{O}{\|}}{C}-\underset{H}{\overset{}{N}}-(CH_2)_{n_3}-\underset{\underset{O}{\|}}{C}-OR_3$$

with R$_1$ = H or —CH$_3$
R$_3$ = H or —CH$_3$
n$_3$ = 1, 2, 3 or 5 or an asymetric N-acryloylaminoacide (or ester) (L series) of the formula:

$$CH_2=\underset{R_1}{\overset{}{C}}-\underset{\underset{O}{\|}}{C}-NH-\underset{R_4}{\overset{*}{CH}}-\underset{\underset{O}{\|}}{C}-OR_3$$

with R$_1$ = H or —CH$_3$

R$_3$ having the same meaning as above $R_4 = -CH_3$ $-CH(CH_3)_2$ $-CH_2(CH_3)_2$

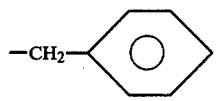

$-CH_2-CH_2-S-CH_3$ $-(CH_2)_4-NH_2$ or the N-acryloyl (L) proline, or its methyl ester of the formula:

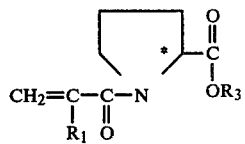

with $R_1$ = H or $-CH_3$ $R_3$ having the same meaning as above.

2. Preparation process of functionalized copolymers of claim 1 wherein the treatment by ethylenediamine is effected between 0° and 25° C.

3. Process according to claim 2 wherein the reaction is effected in the presence of dicyclohexylcarbodiimide, when $R_3$=H.

4. Process according to claim 2 wherein the reaction is effected in the presence of an excess of anhydrous ethylene, when $R_3$=$CH_3$.

5. Process according to claim 2 wherein functionalization degree is comprised between 2 and 5 meq per gram of dry support.

6. Process according to claim 5 wherein the ratio between the number of N-protected aminoacid mols and functionalization degree of support is comprised between 1.1 and 1.2.

* * * * *

UNITED STATES PATENT AND TRADEMARK OFFICE
CERTIFICATE OF CORRECTION

PATENT NO. : 4,436,874
DATED : March 13, 1984
INVENTOR(S) : Christian Aspisi et al.

It is certified that error appears in the above-identified patent and that said Letters Patent are hereby corrected as shown below:

Column 8, the formula between lines 40 and 45 should read:

with $n_2 = 1$ or $2$

Signed and Sealed this

Tenth Day of July 1984

[SEAL]

Attest:

Attesting Officer

GERALD J. MOSSINGHOFF

Commissioner of Patents and Trademarks